US007691056B2

(12) United States Patent
Hirata

(10) Patent No.: US 7,691,056 B2
(45) Date of Patent: Apr. 6, 2010

(54) ENDOSCOPE APPARATUS

(75) Inventor: Yasuo Hirata, Hachioji (JP)

(73) Assignee: Olympus Corporation (JP)

( * ) Notice: Subject to any disclaimer, the term of this patent is extended or adjusted under 35 U.S.C. 154(b) by 943 days.

(21) Appl. No.: 11/012,981

(22) Filed: Dec. 15, 2004

(65) Prior Publication Data

US 2005/0182291 A1    Aug. 18, 2005

(30) Foreign Application Priority Data

Dec. 19, 2003    (JP) .............................. 2003-422692

(51) Int. Cl.
*A61B 1/00* (2006.01)
*A61B 1/04* (2006.01)

(52) U.S. Cl. .................. 600/129; 600/117; 600/175

(58) Field of Classification Search ............... 600/103, 600/117–118, 127, 129, 152, 175, 172, 174, 600/176
See application file for complete search history.

(56) References Cited

U.S. PATENT DOCUMENTS

| 4,469,091 | A | * | 9/1984 | Slanetz, Jr. .................. 600/117 |
| 5,096,669 | A | * | 3/1992 | Lauks et al. ............. 204/403.02 |
| 5,662,587 | A | * | 9/1997 | Grundfest et al. ............ 600/114 |
| 6,086,542 | A | * | 7/2000 | Glowa et al. ................. 600/561 |
| 6,419,626 | B1 | * | 7/2002 | Yoon ........................... 600/109 |
| 6,540,670 | B1 | * | 4/2003 | Hirata et al. ................. 600/152 |
| 6,656,112 | B2 | * | 12/2003 | Miyanaga .................... 600/179 |
| 6,764,441 | B2 | * | 7/2004 | Chiel et al. .................. 600/115 |
| 6,902,528 | B1 | * | 6/2005 | Garibaldi et al. ............. 600/118 |
| 7,104,953 | B2 | * | 9/2006 | Hirata et al. ................. 600/152 |
| 7,282,026 | B2 | * | 10/2007 | Ogawa ........................ 600/172 |
| 2004/0030221 | A1 | * | 2/2004 | Ogawa ........................ 600/175 |
| 2004/0143162 | A1 | * | 7/2004 | Krattiger et al. ............. 600/175 |

FOREIGN PATENT DOCUMENTS

| JP | 58-67231 | 4/1983 |
| JP | S60-88921 | 5/1985 |
| JP | 2-20817 | 1/1990 |
| JP | 5-307145 | 11/1993 |
| JP | 10-108828 | 4/1998 |
| JP | H10-216085 | 8/1998 |
| JP | 2002-191547 | 7/2002 |
| JP | 2002-263057 | 9/2002 |

OTHER PUBLICATIONS

Office Action issued by Japanese Patent Office on Dec. 8, 2009 in connection with corresponding Japanese Patent Application No. 2003-422692.
English translation of Japanese Office Action issued Dec. 8, 2009 submitted as a statement of relevancy of the prior art against instant application.

* cited by examiner

*Primary Examiner*—John P Leubecker
*Assistant Examiner*—Philip R Smith
(74) *Attorney, Agent, or Firm*—Ostrolenk Faber LLP

(57) ABSTRACT

An endoscope apparatus including: an elongated insertion section; an adaptor, which has an illuminating section including optical elements, and an observation optical system, that are attached to and removed from a tip of the insertion section; a sensor provided in the adaptor; and electrical contacts for the illumination section, and electrical contacts for the sensor, provided in the adaptor and the tip of the insertion section.

11 Claims, 13 Drawing Sheets

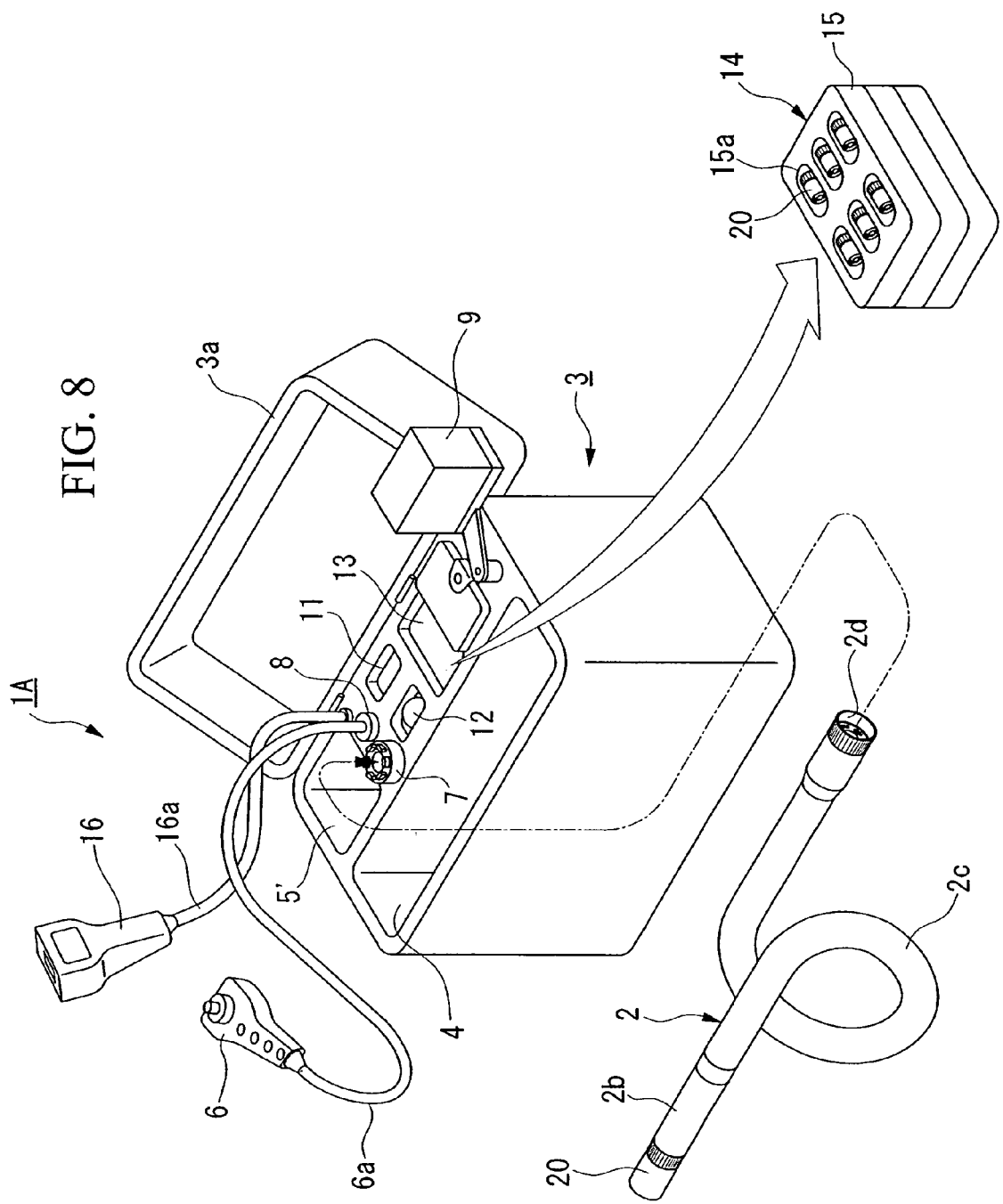

ENDOSCOPE APPARATUS

Priority is claimed on Japanese Patent Application No. 2003-422692, filed Dec. 19, 2003, the contents of which are incorporated herein by reference.

BACKGROUND OF THE INVENTION

1. Field of the Invention

The present invention relates to an endoscope apparatus to be used for industrial, medical, or similar applications, which is provided with a sensor at the tip of an insertion section which is inserted into a cavity.

2. Description of Related Art

Typically, an endoscope apparatus used for an industrial or medical application is provided with an elongated insertion section, which is inserted into a cavity. Furthermore, in such an endoscope apparatus, an illumination device is provided at the tip of the insertion section in order to illuminate the object to be observed in the cavity, for easy observation and imaging. In recent years, light-emitting diodes (referred to hereunder as LEDs) have been proposed for use as such illumination devices (for example, refer to Japanese Unexamined Patent Application, First Publication No. H10-216085).

Moreover, an endoscope apparatus incorporating an elongated insertion section is also disclosed in which an imaging adaptor is installed at the tip of the insertion section such that it can be attached and removed freely, and in which an imager such as a CMOS sensor or the like, and a substrate containing an acceleration sensor, are provided in the imaging adaptor (for example, refer to Japanese Unexamined Patent Application, First Publication No. 2002-263057). The acceleration sensor in this case is provided to detect the direction of gravity.

Incidentally, in the case where LEDs are installed at the tip of the insertion section for use as illumination for observation, temperature control is required to prevent the LED illuminators from being damaged, or the like. Furthermore, in the case where fluid actuators are used for the bending operations of the bending section, it is desirable to measure the pressure of the fluid supplied around the bending section in order to control the bending operation using feedback, and detect leakage of the fluid.

In this manner, it is necessary to provide a range of sensors that can measure required information, such as temperature, pressure, and the like, appropriately.

In addition, for the imaging device for observing an object to be observed, optimum optical lens groups are selected appropriately for use according to various conditions such as the object to be observed, observation range, and the like. Against this background, an imaging device (CCD, CMOS sensor or the like) is provided at the tip of the insertion section, and a plurality of types of adaptor that can be attached and removed are prepared to be exchanged during use. Since the adaptors are provided with illuminating devices (LEDs or the like) and optical lens groups for different applications, the adaptor having the optical lens groups most suited to the observation conditions is selected at the time of actual usage.

In the case where a plurality of types of adaptor are exchanged during use, if the construction is such that the above-described range of sensors is provided in the adaptors, it is anticipated that there will be a variety of combinations of different optical lens groups and sensors.

SUMMARY OF THE INVENTION

A first endoscope apparatus of the present invention includes: an elongated insertion section; an adaptor which has an illuminating section and an observation optical system that are attached to and removed from a tip of the insertion section; a sensor provided in the adaptor; and electrical contacts for the illumination section, and electrical contacts for the sensor, respectively provided in the adaptor and the tip of the insertion section.

Furthermore, a second endoscope apparatus of the present invention includes: an insertion section having an imaging device; an adaptor which is attached to and removed from a tip section of the insertion section, and has an optical lens group for an illuminating device and for observation; and a sensor device which is detachably provided between the adaptor and the tip section, or to the front of the adaptor.

In the above-described second endoscope apparatus, the sensor device may be provided with one or more types of measuring device, and an electrical connection device for this measuring device.

Moreover, the arrangement may be such that the sensor device is provided between the adaptor and the tip section, a bending section of the insertion section is bent by a fluid actuator, and the measuring device is provided with a pressure sensor for measuring the pressure of a fluid driving the fluid actuator.

Furthermore, the sensor device may be provided with a memory device for storing measured values which is measured by the measuring device.

Moreover, a sensor information measuring device may be provided for reading information of the measured values stored in the memory device.

The above-described second endoscope apparatus may further include: an identification signal output device, which is provided in both the adaptor and the sensor device, and outputs unique signals according to the types of the adaptor and the sensor device; and an identification device having a reading and determining device which reads the unique signals, and determines the types of the adaptor and the sensor device.

BRIEF DESCRIPTION OF THE DRAWINGS

FIG. 8 is an overall perspective view of an endoscope apparatus according to a third embodiment.

DETAILED DESCRIPTION OF THE INVENTION

Hereunder are descriptions of embodiments of an endoscope apparatus according to the present invention with reference to the figures.

First Embodiment

A first embodiment of an endoscope apparatus of the present invention will be described with reference to FIG. 1 to FIG. 3B.

Figure 1:
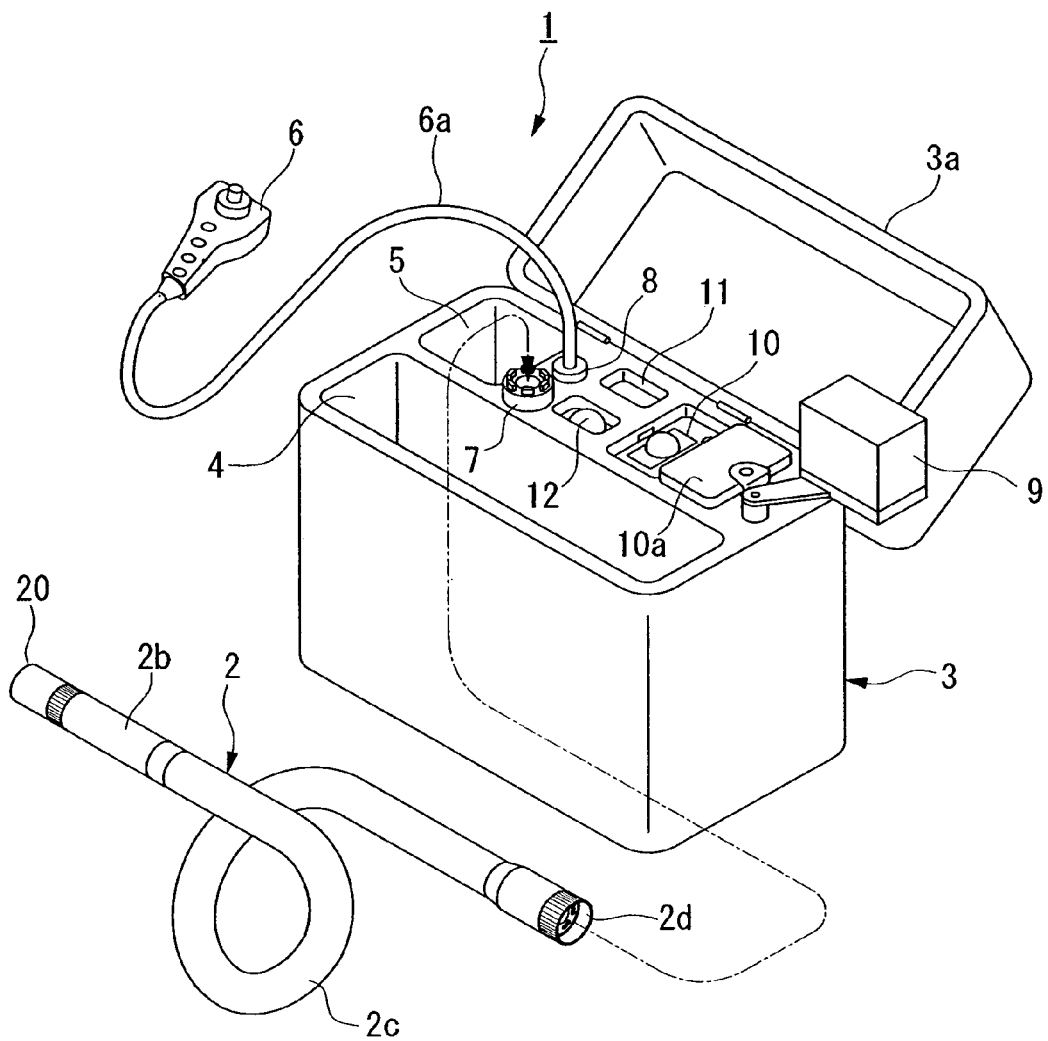
FIG. 1 is an overall perspective view of an endoscope apparatus according to a first embodiment of the present invention.

FIG. 1 is a perspective view showing the overall structure of an endoscope apparatus 1 according to the present embodiment. The endoscope apparatus 1 has an elongated insertion section 2, and a body (referred to hereunder as "endoscope body") 3 to which a proximal end section 2d of the insertion section 2 is connected, as its main structural components.

The endoscope body 3 is formed in an approximately rectangular box shape, and a power source (battery), a range of equipment, a control section and the like, which are not shown in the figure, are built into the case body provided with an opening and closing lid 3a. An insertion section cavity 4, and an operating section cavity 5, are formed in the top face of the endoscope body 3. The insertion section cavity 4 is a space for storing the removed insertion section 2. The operating section cavity 5 is a space for storing a removed operating section 6 and a cable 6a.

The endoscope body 3 is provided with an insertion section connector 7 to which a proximal end section 2d of the insertion section 2 is connected, an operating section connector 8 to which the cable 6a for the operating section 6 for bending the insertion section 2 is connected, a monitor screen 9, such as a liquid crystal display (LCD), for displaying an image, an information measuring section 10 for reading information of a measured value from a sensor substrate, which is described later, and a PC card insertion opening 11. In FIG. 1, reference symbol 12 denotes a cylinder, being a fluid pressure storage device, used when bending the bending section 2b to be described later, and reference symbol 10a denotes an opening and closing cover supported by a hinge or the like such that it opens and closes the information measuring section 10.

Figure 2:
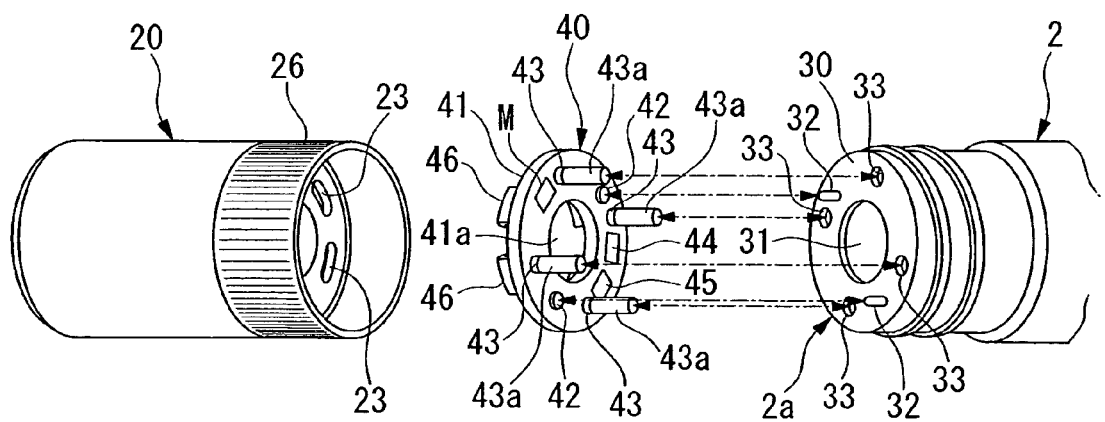
FIG. 2 is an exploded perspective view showing the structure of a tip section of an insertion section of the endoscope apparatus.

The insertion section 2 includes an adaptor 20, a tip section body 2a (refer to FIG. 2), being a rigid tip section, a flexible tube 2c, and the proximal end section 2d, which are connected together. As shown in FIG. 2, the sensor substrate (sensor device) 40 to be described later is a separate unit from the adaptor 20 and the tip section body 2a, and is arranged between the adaptor 20 and the tip section body 2a such that it can be exchanged.

Figure 3A:
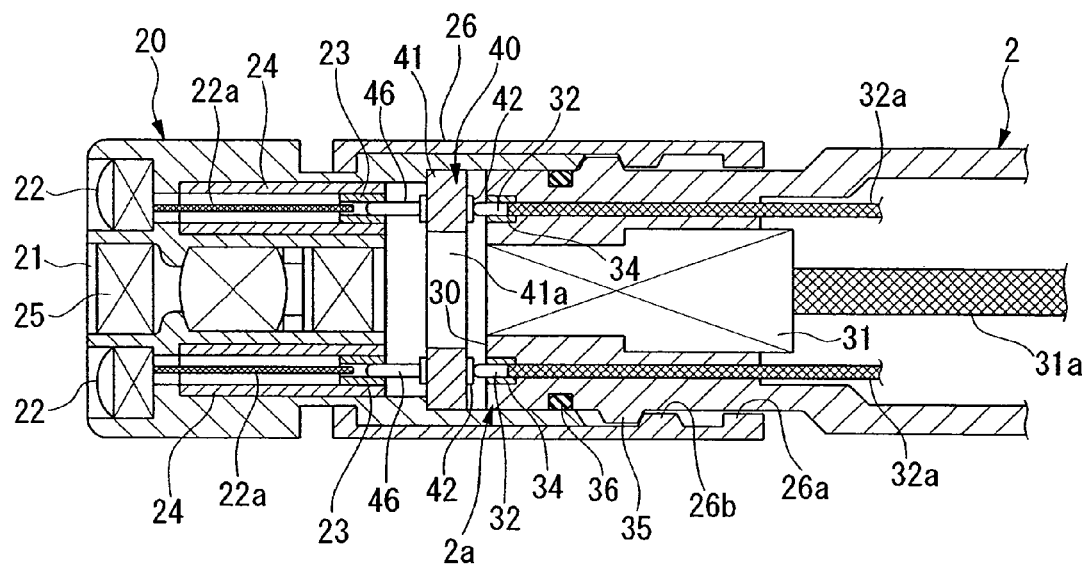
FIGS. 3A and 3B are cross-sectional diagrams to explain LED illuminators provided in the insertion section of the endoscope apparatus, FIG. 3A showing a state when an adaptor is connected, and FIG. 3B showing a state before the adaptor is connected.

As shown in FIG. 3A, an observation window 21 is provided in the central part of the tip face of the adaptor 20, and a plurality of LED illuminators (illuminating devices) 22 is located around the observation window 21. Power is supplied to the LED illuminators 22 via electrical wires 22a. One end of each of the electrical wires 22a is connected to an LED illuminator 22, and the other end is connected to a corresponding through hole shaped electrode 23 formed from conductive material. The electrical wires 22a and electrodes 23 are inserted into corresponding tubular shaped insulating elements 24.

The observation optical lens group 25 is located on the rear side of the observation window 21. The optical lens group 25 picks up an image from the front of the adaptor 20 in conjunction with an imaging device to be described later. There is a plurality of combinations of different optical lens groups depending on the object to be imaged and the purpose of the imaging. That is, a plurality of types of adaptor 20, in which optical lens groups 25 having different optical characteristics are installed, is prepared in advance.

A sleeve 26 is installed on the rear outer periphery of the adaptor 20 in order to fix the adaptor 20 to the tip section body 2a of the insertion section 2. Internal threads 26a and 26b are formed in two places in the axial direction of the inner peripheral surface of the sleeve 26. The internal thread 26a is positioned on the rear end of the sleeve 26, and the other internal thread 26b is positioned at a predetermined spacing from the internal thread 26a on the tip side. Since the internal thread 26a on the rear end is engaged with an external thread 35 on the tip section body 2a side, it functions as a device for preventing the adaptor 20 from becoming detached. The internal thread 26b on the tip side maintains the connection state of the adaptor 20 to the tip section body 2a by threadedly engaging with the external thread 35 of the tip section body 2a side.

Figure 3B:
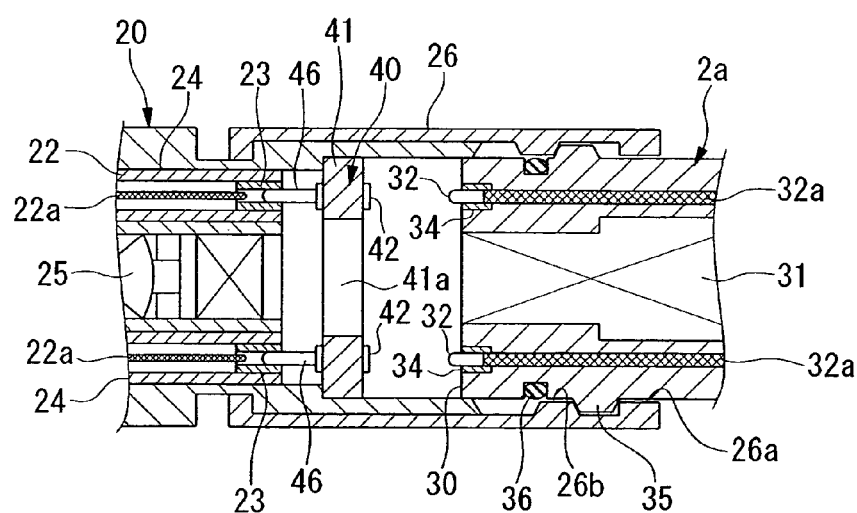
Figure 4:
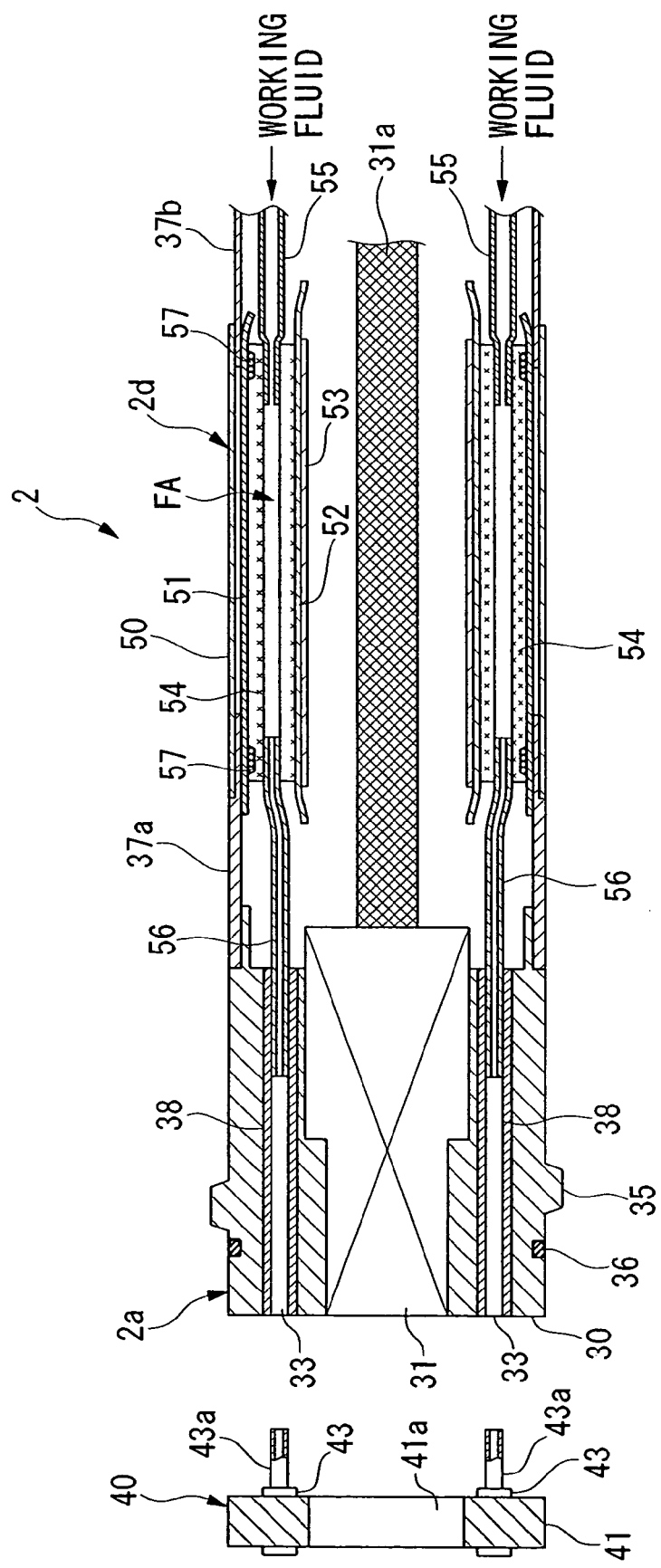
FIG. 4 is a cross-sectional diagram showing the structure in the case of driving a bending section provided in the insertion section of the endoscope apparatus using fluid actuators.

As shown in FIG. 3A, FIG. 3B and FIG. 4, a CCD 31, being an imaging device, a pair of convex electrodes 32, and four pressure ports 33, are arranged in a tip face 30 of the tip section body 2a.

Each of the convex electrodes 32 supplies power from the endoscope body 3 to electrical equipment such as the LED illuminators 22, and a sensor on a sensor substrate 40 to be described later. In the present embodiment, convex electrodes are used, which are enclosed by insulating elements 34 except for their tip sections.

The pressure ports 33 measure the pressure of fluid supplied to fluid actuators FA, being part of the bending section 2b, and have a shape into which convex shaped pressure sensor connectors 43a can be inserted. In the case of bending the bending section 2b in the four directions of upward, downward, to the right, and to the left, four pressure ports 33 are required, whereas in the case of bending in two directions, for example, only two are required.

As shown in FIG. 3A, an O-ring 36 is provided in order to maintain a sealed condition for the interior space of the adaptor 20 and the sensor substrate 40.

As shown in FIG. 3B, the sensor substrate 40 is a disk shaped substrate 41 provided with sensors, being measuring devices, and electrodes, being electrifying devices (the detail will be described hereunder). A through hole 41a in the substrate 41 is an imaging path formed such that it communicates between the optical lens group 25 and the CCD 31.

As shown in FIG. 2, the sensor substrate 40 is provided with a pair of electrodes 42, four pressure sensors 43, an acceleration sensor 44, and a temperature sensor 45 on the side facing the tip face 30. Furthermore, it is provided with LED illuminators 22 and an identical number of convex electrodes 46 on the rear of the side facing the tip face 30. Here, not all of the sensors are required, and the number may be changed appropriately as required. The pair of electrodes 42 are connected electrically to corresponding convex electrodes 46 by a conductive pattern formed on the substrate 41.

As shown in FIG. 3A, by connecting such that the sensor substrate 40 is sandwiched between the adaptor 20 and the tip section body 2a, the electrodes 42 contact the electrodes 32 on the tip face 30 side so as to be connected electrically. In a state in which the sensor substrate 40 is connected to the adaptor 20 at a predetermined position, the convex electrodes 46 are inserted into corresponding electrodes 23 so that current can flow. The convex electrodes 32 on the tip face 30 are connected to the proximal end section 2d via corresponding electrical wires 32a, and furthermore, are connected to the power in the endoscope body 3 by connecting the proximal end section 2d to the insertion section connector 7.

Accordingly, power is supplied to the LED illuminators 22 from the power in the endoscope body 3 via the electrical wires 32a, the convex electrodes 32, the electrodes 42, the convex electrodes 46, the electrodes 23, and the electrical wires 22a.

Hereunder is a description of the objectives of providing the above-mentioned sensors, being measuring devices.

The pressure sensors 43 measure the pressure of the working fluid (for example, nitrogen gas or the like) supplied to the fluid actuators FA, being part of the bending section 2b. It is possible to use the measured values of the fluid pressure for feedback control when bending the bending section 2b. The fluid actuators FA in the bending section 2b are, as shown in FIG. 4, installed between a front ferrule 37a connected to the tip section body 2a, being a rigid tip section, and a rear ferrule 37b connected to the flexible tube 2c.

The fluid actuator FA has a construction in which an internal tube 52 and an internal coiled tube 53 are inserted into an external coiled tube 50 and an external tube 51, which are joined such that they sandwich the front ferrule 37a and the rear ferrule 37b, and a multi lumen tube 54 is provided between the internal tube 52 and the external tube 51.

The multi lumen tube 54 is formed from soft silicon material, and is an element having an approximately circular cross section, in which a plurality of air chambers is provided at equal pitch spacing (for example, four places at a 90 degree pitch). One end of each of the air chambers is connected to a corresponding working fluid supply tube 55, and the other end is connected to a connecting tube 56. One end of each of the working fluid supply tubes 55 is connected to the cylinder 12 of the endoscope body 3, and supplies working fluid to a corresponding air chamber of a multi lumen tube 54. At the other side, one end of each of the connection tubes 56 is connected to a corresponding connecting tube 38 made of an elastic material, installed such that it passes through the tip section body 2a in its axial direction.

The external coiled tube 50 and the internal coiled tube 53 are stainless steel tubular elements for example, which bend easily. The external tube 51 and the internal tube 52 are fluorine thin walled tubes for example, for preventing the multi lumen tubes 54 from being damaged by being sandwiched between the external coiled tube 50 and the internal coiled tube 53. Reference symbol 57 as shown in FIG. 4 denotes a rolled thread for fixing the multi lumen tubes 54.

When the sensor substrate 40 is mounted at a predetermined location on the tip face, the pressure sensor connectors 43a are inserted into corresponding connecting tubes 38 by means of the pressure ports 33. Since the connecting tubes 38 are elastic, the inner peripheral surface of the connecting tubes 38 and the outer peripheral surface of the pressure sensor connectors 43a fit tightly so as to prevent the working fluid from leaking. Accordingly, the pressure of the working fluid supplied to the multi lumen tube 54 acts on corresponding pressure sensors 43 via four sets of the connection tube 56, the connecting tube 38, and the pressure sensor connector 43a. Therefore, it is possible for the pressure sensors 43 to measure the pressure of the working fluid actually supplied.

Since the fluid actuators FA bend due to the air chambers on one side, inside the multi lumen tubes 54, expanding and becoming longer due to the supply of working fluid, it is possible to bend the bending section 2b in a desired direction by supplying working fluid to the air chambers on the opposite side (180 degrees) from the direction in which it is to bend.

By sending the values of pressure measured by the pressure sensors 43 to a control section of the endoscope body 3 in real time via signal lines (not shown in the figure) or the like, which are arranged so as to line up with the electrical wires 32a for power supply, it is possible to control the fluid actuators FA using feedback, in which the pressure of the working fluid supplied changes according to the operation of the operating section 6.

Furthermore, instead of sending the values of the pressure measured by the pressure sensors 43 in real time, and executing feedback control, the arrangement may be such that as shown in FIG. 2 for example, a memory M, being a storage medium (storage device), is provided in the sensor substrate 40, and the measured values are stored in the memory M in response to a manual operation of the operating section 6, or the measured values are stored in the memory M at a predetermined time.

Moreover, the arrangement may be such that in the case of a predetermined normal measured value, it is not stored, and in the case where an abnormal value, which exceeds a threshold, is measured, it is stored automatically. In this case, it is preferable to store the abnormal value with its location by providing an IC chip alongside (not shown in the figure) that has a GPS function. Furthermore, the arrangement may be such that a warning signal can be output as required in the case of an abnormality occurring due to breakage.

The pressure sensor 43 can monitor breakage of the multi lumen tube 54, leakage of working fluid, or the like, by establishing its location and the like appropriately, and furthermore, can be used for watertightness checks.

The acceleration sensor 44 can be used for such functions as: detecting the direction of gravity acting on the insertion section 2, monitoring impacts acting on the tip section of the insertion section 2, and measuring the position (insertion amount) to which the tip of the insertion section 2 is inserted. That is, since the acceleration sensor 44 can also perform GPS functions, it is possible to pinpoint the location of an abnormality detected on the screen.

It is possible to use the values measured by the temperature sensor 45 for control, or the like, of the temperature of the LED illuminators 22, for example.

Moreover, if a humidity sensor is provided for example in the sensor substrate 40, in order to monitor the water content of the working fluid, it is possible to prevent a malfunction of the fluid actuators FA, which can occur due to the working fluid containing a lot of water.

By using a sensor substrate 40, which is a separate item from the adaptor 20, and by installing a plurality of different types of measuring device (sensors) in the sensor substrate 40, and thus by combining a plurality of adaptors 20 having different optical lens groups 25, and a plurality of sensor substrates 40 having different measuring devices, it is possible to construct a variety of adaptors 20 easily. Accordingly, compared with the case of many types of adaptor having different optical lens groups 25 and measuring devices, it is possible to reduce the number of adaptors 20. Furthermore, since the sensor substrate 40 is smaller than the adaptor 20, it is easy to find storage space. Moreover, since the number of adaptors 20 is reduced, and the sensor substrate 40 is miniaturized, it is also possible to improve the portability of the endoscope apparatus 1.

Figure 5:
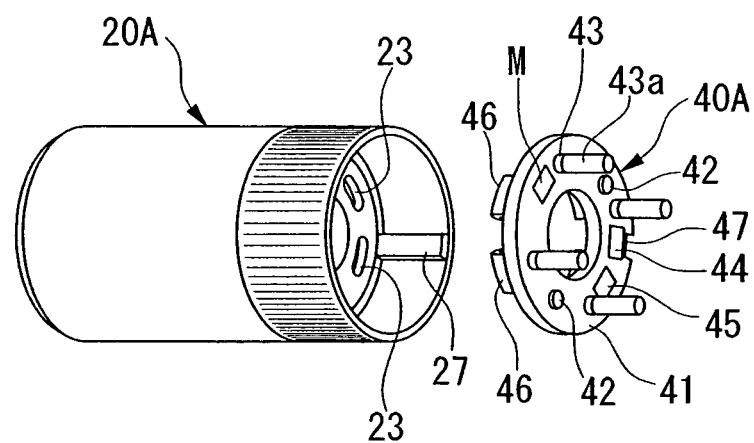
FIG. 5 is a diagram showing a first modified example of the insertion section of the endoscope apparatus, being an exploded perspective view of the adaptor.

Next is a description of a first modified example of the first embodiment based on FIG. 5. The same reference symbols are used for the same elements as in the first embodiment, and descriptions thereof are omitted.

In the present first modified example, a guide ridge 27 is provided in the axial direction on the inner peripheral surface of an adaptor 20A, and a notch section 47 with a similar shape to the cross sectional shape of the ridge 27 is formed in the outer peripheral surface of a sensor substrate 40A. By so doing, when the sensor substrate 40A is pushed into the adaptor 20A, the notch section 47 is guided along axially by engaging with the guide ridge 27, and thus it is possible to guide the convex electrodes 46 on the sensor substrate 40A side toward corresponding electrodes 23 smoothly, so as to be inserted therein. That is, since it is possible to position the sensor substrate 40A on the adaptor 20A, it is possible to insert the sensor substrate 40A easily and accurately for smooth installation.

Figure 6:
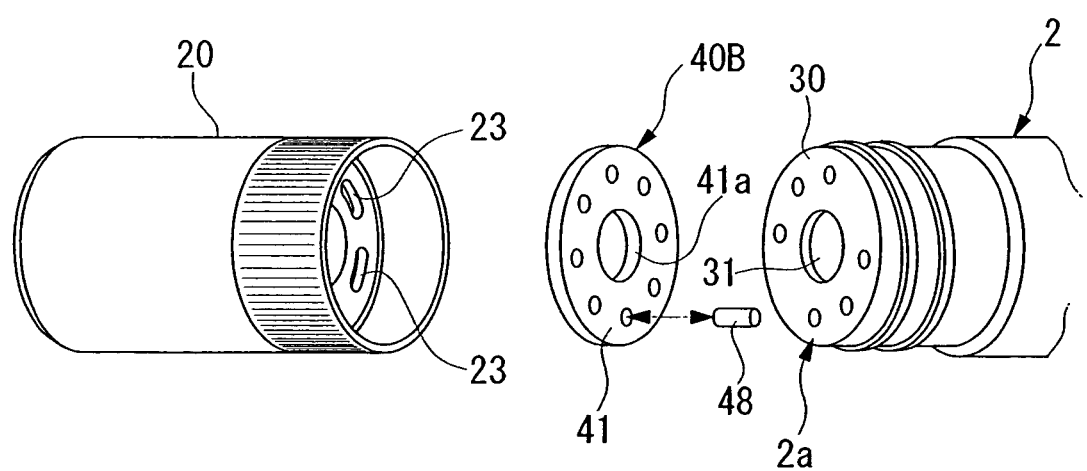
FIG. 6 is a diagram showing a second modified example of the insertion section of the endoscope apparatus, being an exploded perspective view of the adaptor.

Next is a description of a second modified example of the first embodiment based on FIG. 6. The same reference symbols are used for the same elements as in the first embodiment, and descriptions thereof are omitted.

In the present second modified example, IC chips 48 are installed as identification signal output devices. The IC chips 48 output unique signals, which are different for each type of sensor substrate 40B, and by using a determination device (not shown in the figure) such as a scanner or the like alongside, which reads these unique signals, it is possible to identify many types of sensor substrate 40B, whose appearances are similar, easily and accurately.

That is, a sensor substrate 40B of the present modified example is provided with a sensor substrate identification device for reading a unique signal from the IC chip 48, which differs depending on the type, by the determination device, and determining its type.

Second Embodiment

Figure 7A:
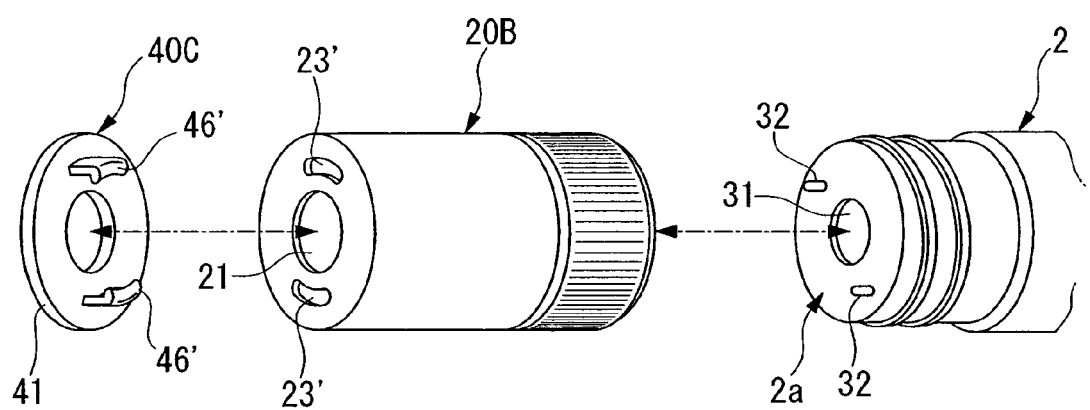
FIGS. 7A and 7B are diagrams showing a second embodiment of the endoscope apparatus according to the present invention, FIG. 7A being a perspective view of the tip section of the insertion section, and an adaptor, and FIG. 7B being a perspective view of a sensor substrate viewed from its front side.
Figure 7B:
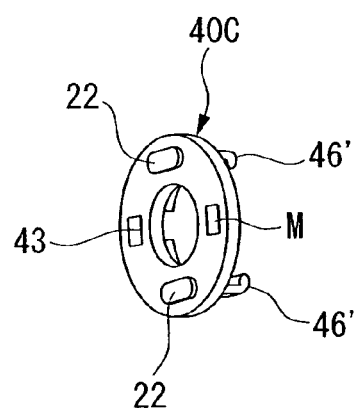

Next is a description of a second embodiment of the present invention based on FIG. 7A and FIG. 7B. The same reference symbols are used for the same elements as in the first embodiment, and descriptions thereof are omitted.

The present embodiment uses a construction in which a sensor substrate 40C can be installed at the tip face of an adaptor 20B such that is can be attached and removed freely. The sensor substrate 40C is provided with a pressure sensor 43, a memory M, and a pair of LED illuminators 22, for example, on the front side in the direction of insertion. Furthermore, a pair of convex electrodes 46' is provided on the face of the sensor substrate 40C, facing the adaptor 20B, which is connected electrically by being inserted into a pair of electrodes 23' on the adaptor 20B.

In the case of using this construction, a measuring device such as a pressure sensor 43 or the like is installed on the tip face of the insertion section 2. In this case, for a measuring device to be installed in the sensor substrate 40C, similarly to the first embodiment, it is possible to make an appropriate choice from among pressure sensors, acceleration sensors, temperature sensors, and the like, and install one or more of them. The measurements of these sensors differ depending on their locations. Furthermore, power is supplied to electrical equipment such as the pressure sensor 43, the memory M, the LED illuminator 22, and the like, via the electrodes 23' of the adaptor 20B and the convex electrodes 46'. Here, the adaptor 20B and the insertion section 2 are connected by connecting the convex electrodes 32 on the insertion section 2 to electrodes (not shown in the figure) on the adaptor 20B. Thus the electrical equipment is connected to the power in the endoscope body 3.

It is possible to measure the environment of a cavity, being an object to be observed, by installing a measuring device on the tip face side of the adaptor 20B. That is, in addition to an image by an imaging device, it is possible to measure the internal environment such as temperature, pressure, humidity, and the like, of the cavity to be observed, depending on the type of measuring device installed.

In the case where an acceleration sensor is included in the measuring device, even if the locations where each of the sensors are installed are changed, there is no change in the physical items to be measured, and hence it is possible to perform similar measurement to the first embodiment.

Third Embodiment

Next is a description of a third embodiment of the present invention based on FIG. 8. The same reference symbols are used for the same elements as in the first embodiment, and descriptions thereof are omitted.

In an endoscope apparatus 1A of the present embodiment, an adaptor storage section 13 is provided in the location of the information measuring section 10 shown in FIG. 1. The adaptor storage section 13 is a space for storing a set of adaptors 14, which is a collection of a plurality of different, grouped adaptors 20. The set of adaptors 14 is stored in the adaptor storage section 13 in a state in which a plurality of storage trays 15, containing a plurality of formed cavities (six in the example in the figure) 15a, is stacked in a plurality of tiers (three tiers in the example in the figure). The arrangement may be such that the adaptors 20 and the sensor substrates 40 are combined and stored in the cavities 15a, or stored separately in dedicated storage cavities that are made to match the shapes of the adaptors 20 and the sensor substrates 40.

Furthermore, in the present embodiment, a scanner 16 is provided instead of the information measuring section 13. The scanner 16 is connected to an endoscope body 3 via a cable 16a, and can read information from the memory M of the sensor substrate 40. The scanner 16 is stored in an operating section cavity 5' together with an operating section 6 when not in use.

According to the endoscope apparatus 1A of the present embodiment, a variety of adaptors 20 and sensor substrates 40 can be stored in the endoscope body 3 efficiently, and can be carried easily by closing an opening and closing lid 3a. Moreover, since the insertion section 2, the operating section 6, and the scanner 16 can be stored in the endoscope body 3, it is possible to find space to store the endoscope apparatus 1A easily, and it is extremely portable.

Fourth Embodiment

Figure 9:
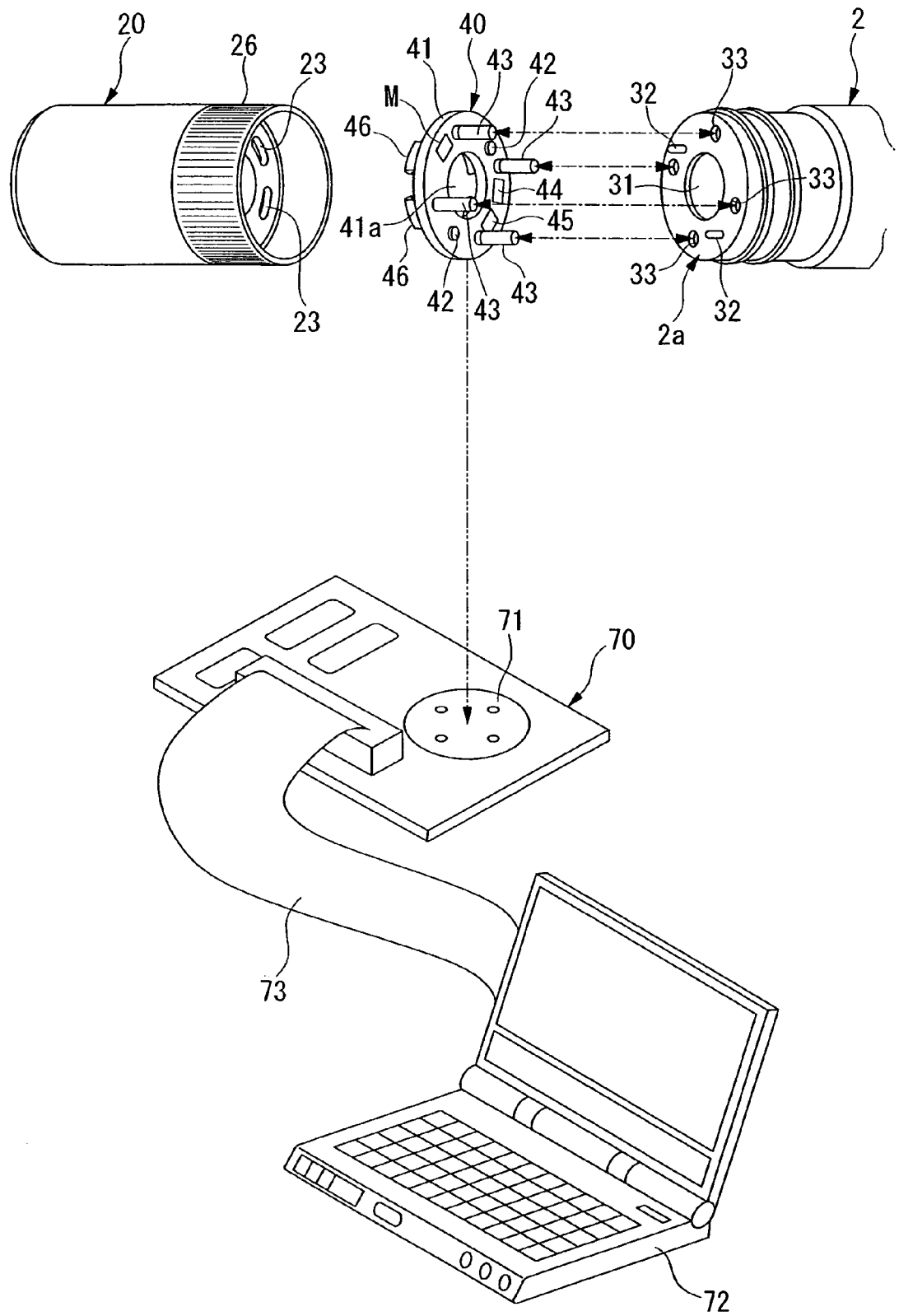
FIG. 9 is a perspective view showing a system containing an endoscope apparatus according to a fourth embodiment of the present invention.
Figure 10:
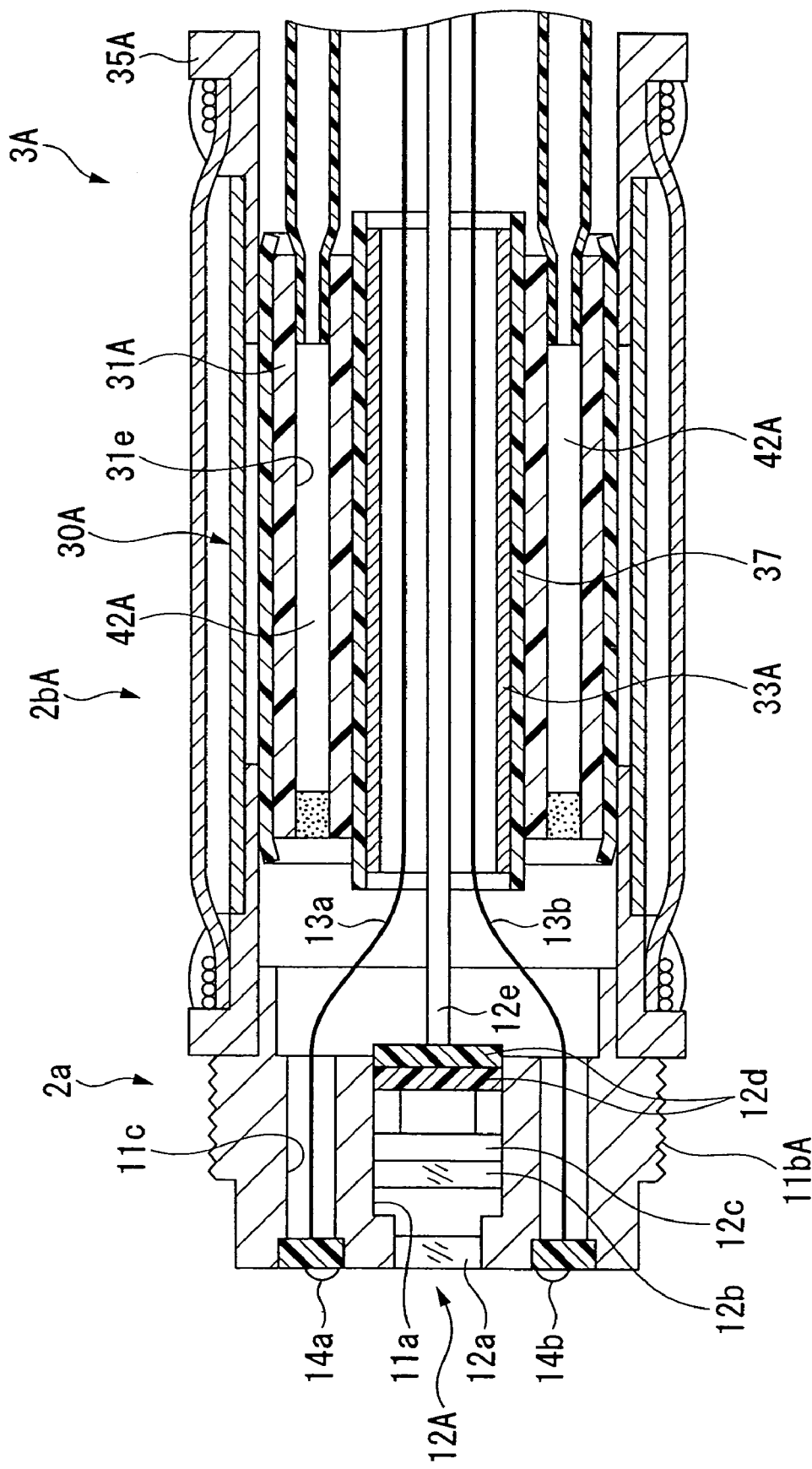
FIG. 10 is a cross-sectional diagram of the tip section of the insertion section of an endoscope apparatus according to a fifth embodiment of the present invention.

Next is a description of a fourth embodiment of the present invention based on FIG. 9. The same reference symbols are used for the same elements as in the first embodiment, and descriptions thereof are omitted.

In the present embodiment, an analysis substrate 70, and an analyzer 72, being separate items from a sensor substrate 40, are provided as devices for reading and analyzing measured results stored in a memory M of the sensor substrate 40. The analysis substrate 70 is provided with a mounting section 71 onto which the sensor substrate 40 is mounted, and the mounting section 71 is provided with a sensor information measuring device such as a scanner or the like, for example.

As the analyzer 72, a personal computer or the like is used. A signal cable 73 is connected between the analyzer 72 and the analysis substrate 70, and the sensor substrate 40 is installed on the mounting section 71. As a result, it is possible to read the measured results stored in the memory M of the sensor substrate 40 using the analyzer 72 for a range of analysis.

Moreover, by analyzing the measured results stored in the memory M, it is possible to determine the conditions (observation environment such as temperature, pressure, or the like) when the insertion section 2 is used. Furthermore, if the insertion section 2 fails, it is possible to obtain evidence in order to investigate the cause of the failure by analyzing the measured results.

Moreover, since the sensor substrate 40 can be attached to and removed from the adaptor 20, it is also possible to continue observations using the insertion section 2 by installing another sensor substrate 40 in the adaptor 20, at the same time as analyzing the measured results.

Furthermore, in the case where the same places are reexamined, it is also possible to perform the observation operation while comparing with historical measured results.

Fifth Embodiment

Hereunder is a description of a fifth embodiment of the present invention with reference to FIG. 10 through FIG. 14. The following description focuses principally on the differences from the first embodiment. The same reference symbols are used for the same elements as in the first embodiment, and descriptions thereof are omitted.

A tip section body 2a, being a rigid tip section, is placed at the tip of a bending section 2bA, which incorporates fluid pressure actuators 30A. A central through hole 11a with a stepped shape is formed in the tip section body 2a to house an image pickup device 12A, being an imaging device. The image pickup device 12A is provided with a lens cover 12a for the apparatus, a cover glass 12b, a CCD 12c, and a substrate 12d. An imaging cable 12e extends from the proximal end section of the image pickup device 12A. The imaging cable 12e is inserted into an internal coil 33A which covers the inner peripheral surface of an internal tube 37 installed in the bending section 2bA.

Furthermore, a pair of tip section element contacts 14a, being electrical contacts for optical elements, is provided in the tip section body 2a. A pair of electrical wires 13a and 13b for supplying power to LED illuminators 22A installed in an adaptor 20C, which is described later, are respectively connected to the tip section element contacts 14a and 14b respectively. The tip section element contacts 14a and 14b are placed in a pair of first contact through holes 11c having a stepped shape, which are in the tip section body 2a. The electrical wires 13a and 13b are also inserted in the internal coil 33A similarly to the imaging cable 12e.

A rear ferrule 35A is fitted, which is associated with the outer circumference of a joining ferrule that is not shown in the figure, provided on the tip section of the flexible tube 2c, and thus the flexible tube 2c is connected to the proximal end side of the bending section 2bA.

Moreover, in the present embodiment, four through holes (not shown in the figure) are arranged regularly around the central through hole 31e of the multi lumen tube 31A. Since the number of through holes is set according to the bending direction of the bending section 2bA, the shape in which it is to be formed, and the like, it is not limited to four, and may be more than four, or fewer than four.

The adaptor 20C is attached to and removed from an external screw section 11bA, to which an internal screw section 24b (to be described later) of the adaptor 20C is also screwed.

Next is a description of the structure of the adaptor 20C with reference to FIGS. 11A to 11D.

The adaptor 20C is provided with a plurality of LED illuminators 22A, being illuminating parts formed from optical elements, and a pressure sensor and a temperature sensor (to be described later), being sensors. Corresponding to the pressure sensors and the temperature sensor, which are provided in addition to the LED illuminators 22A, the tip section body 2a is provided with electrical contacts for sensors (to be described later) corresponding to the pressure sensors and the temperature sensor, in addition to the tip section element contacts 14a and 14b.

Figure 11A:
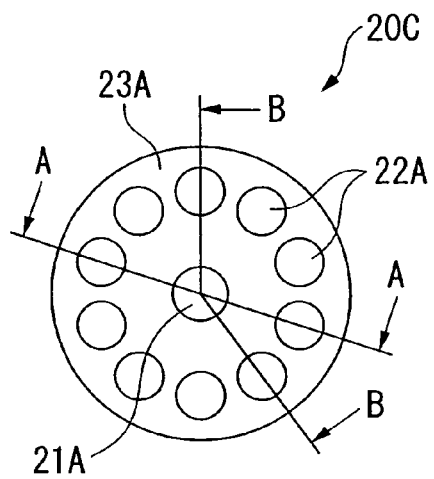
FIG. 11A is a front view of the adaptor of the endoscope apparatus.
Figure 11B:
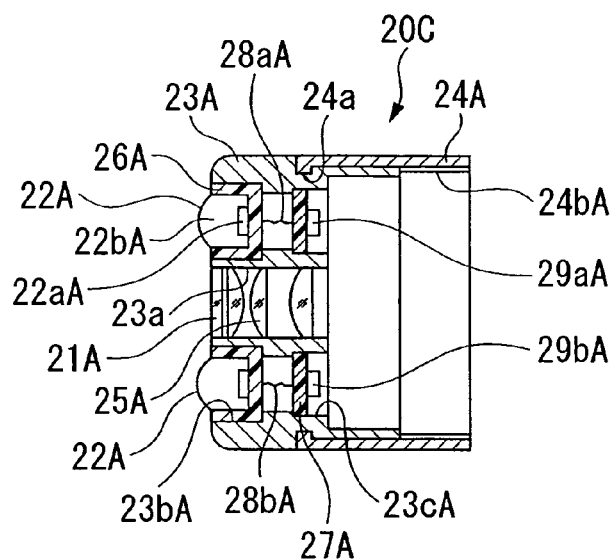
FIG. 11B is a cross-sectional diagram through A-A of FIG. 11A.

As shown in FIG. 11A and FIG. 11B, the adaptor 20C is provided with an adaptor body 23A, and a connecting tube 24A which is connected to the adaptor body 23A such that it can rotate freely. An engagement hook 24a for engaging with a cavity section formed around the peripheral face of the adaptor body 23A is formed on the tip section on the tip side of the connecting tube 24A. An internal screw section 24bA, which screws onto the external screw section 11bA, is formed in the inner peripheral surface of the rear end of the connecting tube 24A.

A central through hole 23a is formed along the axis of the central part of the adaptor body 23A. An imaging lens cover 21A, and an imaging optical lens group 25A including a plurality of optical lenses, which together include an imaging optical system, are provided in the central through hole 23a.

Ten LED illuminators 22A, for example, for which the amount of illuminating light, illumination distance, and the like, are considered in advance, are provided in the periphery of the tip face side of the imaging lens cover 21A. Each of the LED illuminators 22A is provided with an LED 22aA, being a light emitting diode, and a filler for sealing the LED 22aA. The LEDs 22aA are arranged at equal spacing on an LED substrates 26A. The LED substrates 26 are provided in first cavities 23bA formed in the tip face side of the adaptor body 23A. Furthermore, an adaptor substrate 27A to be described later is provided in the periphery of the proximal end of the imaging optical lens group 25A. The adaptor substrate 27A is arranged in a second cavity 23cA formed in the adaptor body 23A.

The electrical wires 28aA and 28bA are electrically connected at one end to a pair of electrode elements, which are not shown in the figure, and are electrically connected at their other end to the front face side of the adaptor substrate 27A. Moreover, adaptor side LED contacts 29aA and 29bA, which are optical device electrical contacts installed on the adaptor 20C side corresponding to the tip section element contact 14*a* and the tip section element contact 14*b*, are provided on the rear side of the adaptor substrate 27A.

Figure 11C:
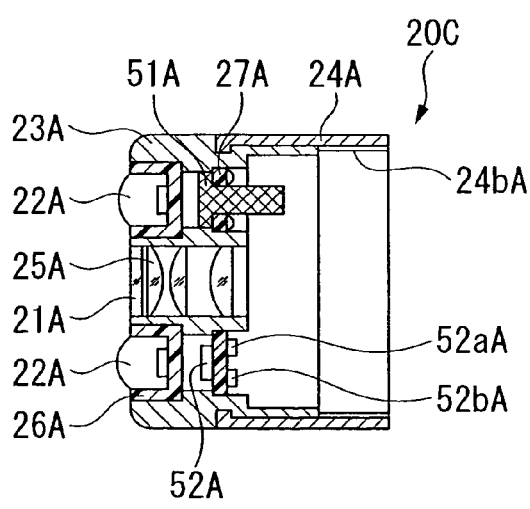
FIG. 11C is a cross-sectional diagram through B-B of FIG. 11A.

As shown in FIG. 11C, pressure sensors 51A for measuring the pressure of the air in each fluid chamber of the fluid pressure actuators 30A, and a temperature sensor 52A for measuring the temperature of the internal space of the tip section body 2*a*, which changes according to the amount of heat generated by the LED illuminators 22A, are arranged on the adaptor substrate 27A.

Figure 11D:
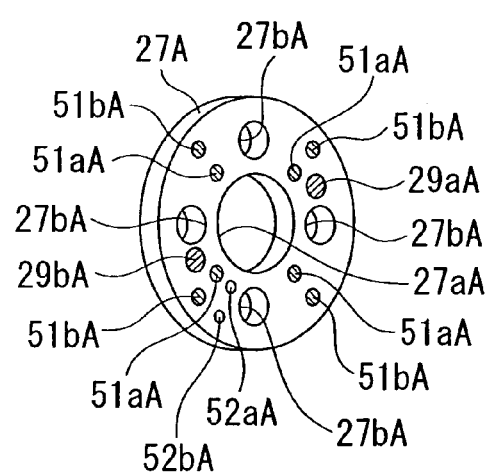
FIG. 11D is a perspective view of an adaptor substrate installed in the adaptor.

As shown in FIG. 11D, the adaptor substrate 27A is a circular plate having a central through hole 27*a*A. The rear face of the adaptor substrate 27A is provided with sensor arrangement through holes 27*b*A for arranging the pressure sensors 51 in the horizontal and vertical directions, the adaptor side LED contacts 29*a*A and 29*b*A, the adaptor side temperature sensor contacts 52*a*A and 52*b*A for outputting values measured by the temperature sensor 52A, adaptor side pressure sensor power contacts 51*a*A for supplying driving power to the pressure sensors 51A, and adaptor side pressure sensor output contacts 51*b*A for outputting values measured by the pressure sensors 51A, in respective predetermined locations.

Figure 12A:
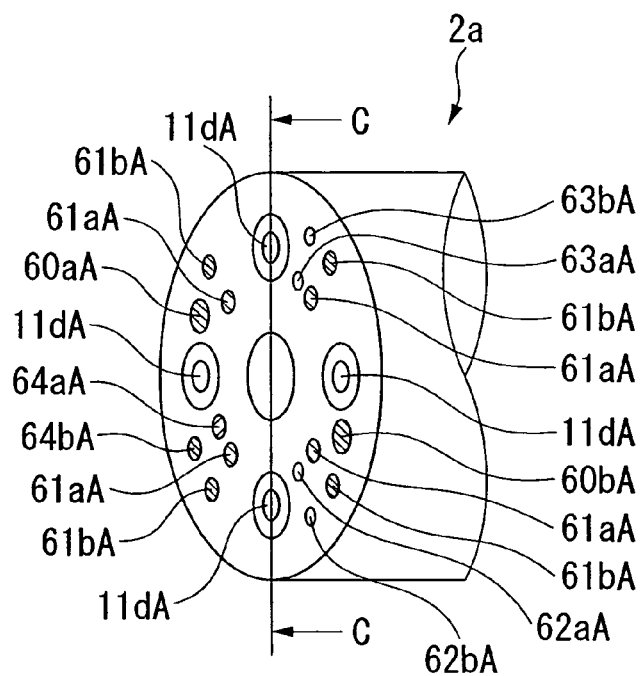
FIG. 12A is a perspective view showing the tip section of the insertion section of the endoscope apparatus.
Figure 12B:
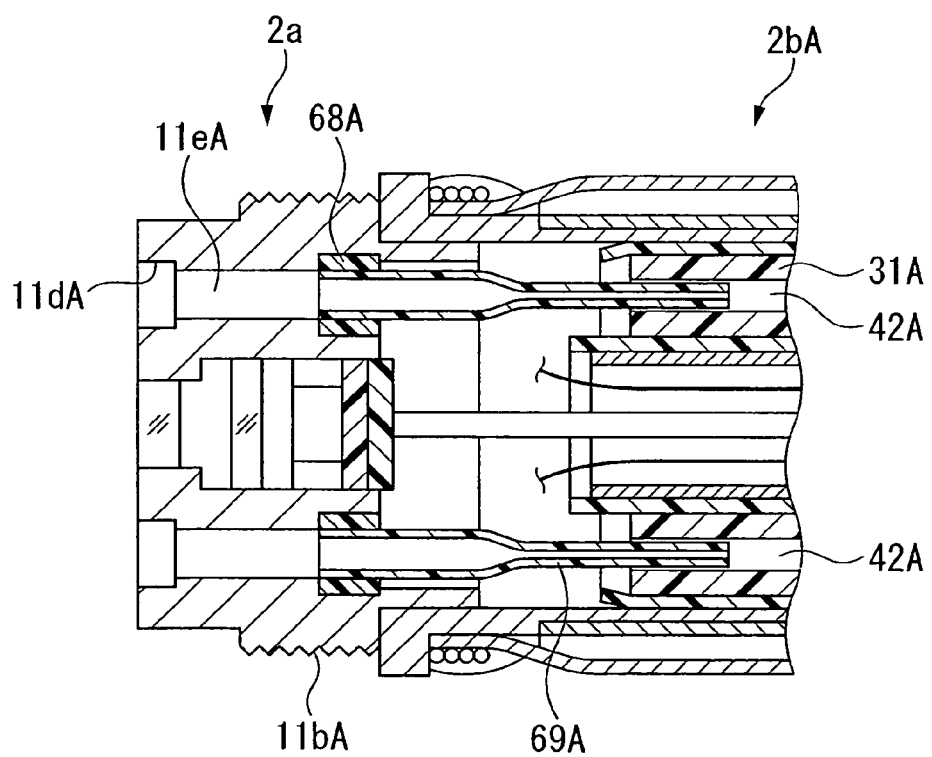
FIG. 12B is a cross-sectional diagram through C-C of FIG. 12A.

The following is a description of the structure of the tip section body 2*a*, which the adaptor 20C is attached to and removed from, with reference to FIG. 12A and FIG. 12B.

The tip face of the tip section body 2*a*, being a rigid tip section, is provided with pressure measurement holes 11*e*A, being through holes having apertures 11*d*A to which the proximal ends of the pressure sensors 51A are inserted, tip section side LED contacts 60*a*A and 60*b*A, tip section side temperature sensor contacts 62*a*A and 62*b*A, tip section side pressure sensor power contacts 61*a*A, and tip section side pressure sensor output contacts 61*b*A, associated with the pressure sensors 51A.

The tip section side LED contacts 60*a*A and 60*b*A are provided in locations facing the adaptor side LED contacts 29*a*A and 29*b*A respectively. The tip section side temperature sensor contacts 62*a*A and 62*b*A are provided in locations facing the adaptor side temperature sensor contacts 52*a*A and 52*b*A respectively. The tip section side pressure sensor power contacts 61*a*A are provided in locations facing the adaptor side pressure sensor power contacts 51*a*A of the pressure sensors 51A. The tip section side pressure sensor output contacts 61*b*A are provided in locations facing the adaptor side pressure sensor output contacts 51*b*A of the pressure sensors 51A.

One end of each of the communicating tubes 69A is connected to the proximal end section of respective pressure measurement holes 11*e*A such that they communicate. The other end of each of the communicating tubes 69A communicates with the tip section side of the fluid chambers 42A of the fluid pressure actuators 30A. As a result, the pressure measurement holes 11*e*A and the fluid chambers 42A are communicated via the communicating tubes 69A.

The proximal end sections of the pressure measurement holes 11*e*A are provided with watertightness maintaining components 68A formed for example from elastic components such as rubber elements or the like. The watertightness maintaining components 68A tightly contact the outer peripheral surface of the communicating tubes 69A and the inner peripheral surface of the pressure measurement holes 11*e* to maintain the watertightness. The rear of each of the communicating tubes 69A has a tapered shape that tapers off towards the proximal end, and is glued in contact with the multi lumen tube 31A.

Figure 13A:
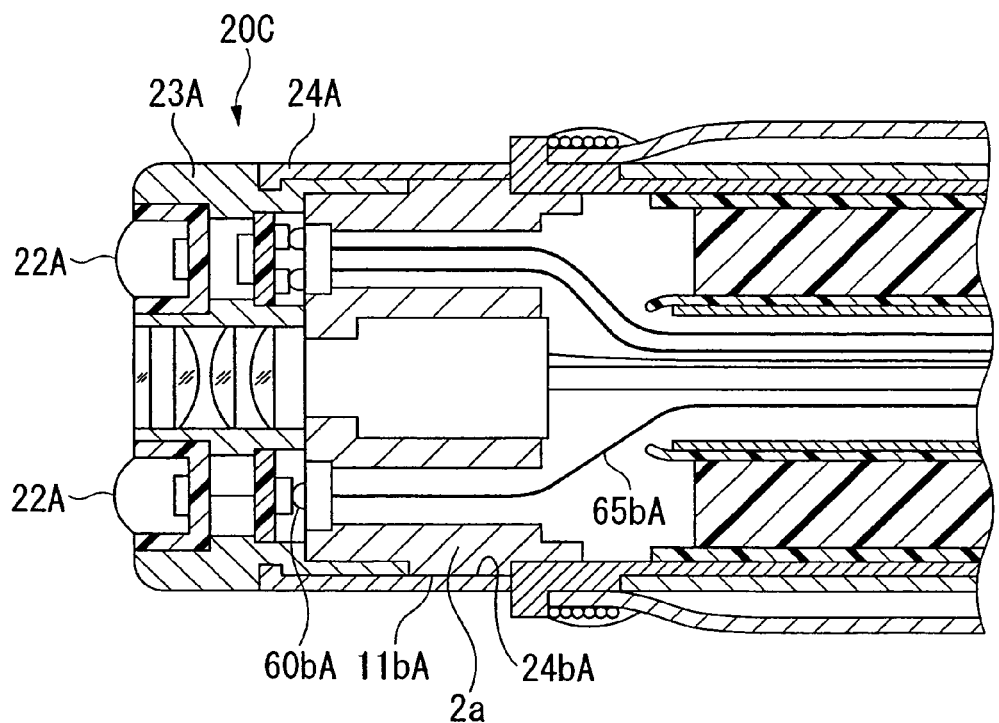
FIGS. 13A and 13B are diagrams showing a state in which the adaptor is mounted on the tip section of the insertion section, being cross-sectional diagrams showing different cross sections.
Figure 13B:
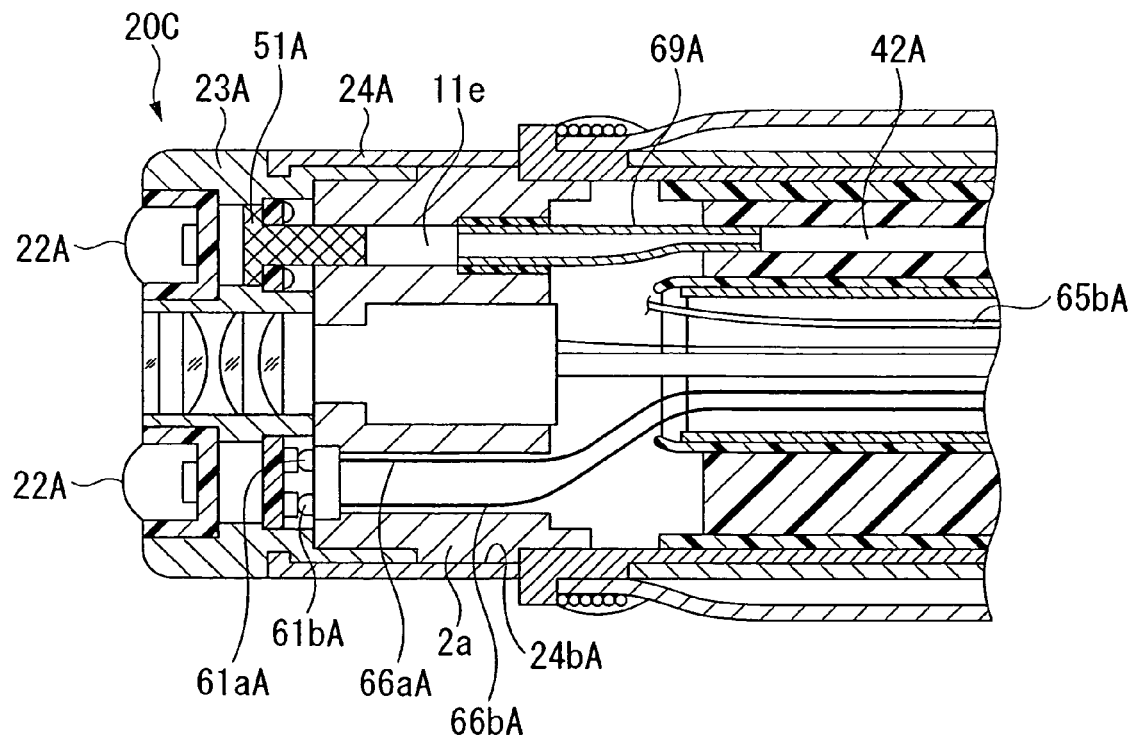
Figure 14:
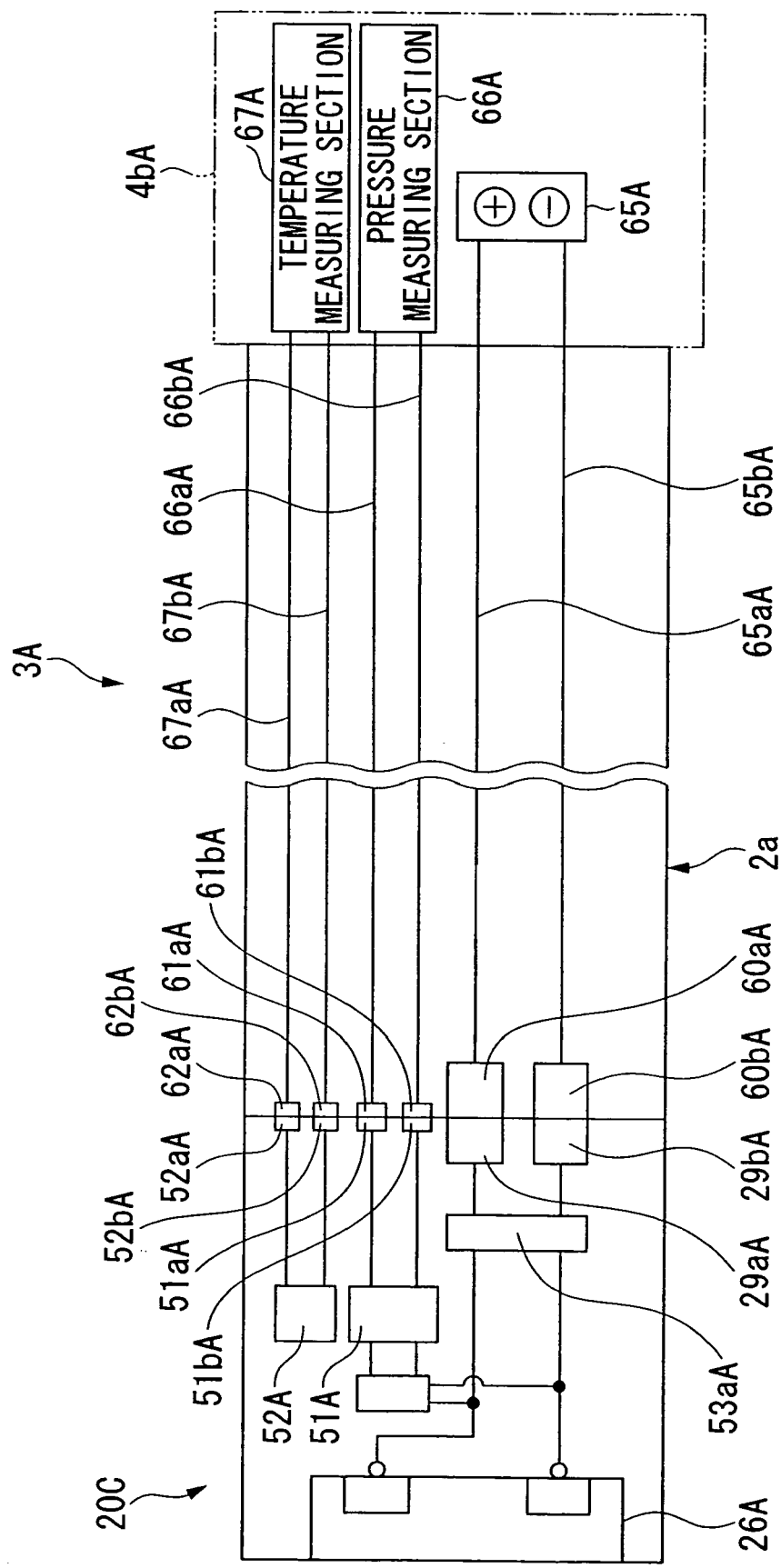
FIG. 14 is a wiring diagram of a part of the endoscope apparatus.

As shown in FIG. 13A, 13B and FIG. 14, electrical wires 65*a*A and 65*b*A extend from the tip section side LED contacts 60*a*A and 60*b*A, and are electrically connected to a battery 65A installed in an insertion section winding section 4*b*A. Similarly, signal lines 67*a*A and 67*b*A extend from the tip section side temperature sensor contacts 62*a* and 62*b*, and are electrically connected to a temperature measuring section 67A in the insertion section winding section 4*b*A. As shown in FIG. 13B and FIG. 14, signal lines 66*a*A and 66*b*A extend from tip section side pressure sensor power contacts 61*a*A and tip section side pressure sensor output contacts 61*b*A, corresponding to the pressure sensors 51A, and are electrically connected to a pressure measuring section 66A provided in the insertion section winding section 4*b*A.

Reference symbols 63*a*A and 63*b*A as shown in FIG. 12A denote tip section side external temperature sensor electrical contacts for measuring external temperature, being the external environment near the tip section. Furthermore, reference symbol 64*a*A denotes an electrical contact for supplying driving power to a tip section side external pressure sensor, which measures external pressure, being the external environment near the tip section. Moreover, reference symbol 64*b*A denotes an electrical contact for outputting values measured by the tip section side external pressure sensor. In this manner, electrical contacts for a range of sensors, and electrical contacts for optical devices, are provided in predetermined locations of the tip face of the tip section body 2*a*.

Next is a description of an endoscope 3A, which is constructed by screwing the tip section body 2*a* and the adaptor 20C together, with reference to FIG. 13A, FIG. 13B, and FIG. 14.

When installing the adaptor 20C, firstly, the relative positions of the adaptor 20C and the tip section body 2*a* are aligned. Next, the internal screw section 24*b*A on the adaptor 20C is screwed into the external screw section 11*b*A on the tip section body 2*a*. As a result, the adaptor 20C is screwed onto and fixed to the tip section body 2*a*, such that the endoscope 3A is assembled.

As shown in FIG. 14, by screwing the adaptor 20C into the tip section body 2*a* to integrate them, the tip section side LED contacts 60*a*A and 60*b*A, and the adaptor side LED contacts 29*a*A and 29*b*A are electrically connected. Furthermore, the tip section side temperature sensor contacts 62*a*A and 62*b*, and the adaptor side temperature sensor contacts 52*a*A and 52*b*A, are electrically connected. Moreover, the tip section side pressure sensor power contacts 61*a*A, and the adaptor side pressure sensor power contacts 51*a*A, are electrically connected. Furthermore, the tip section side pressure sensor output contacts 61*b*A, and the adaptor side pressure sensor output contacts 51*b*A, are electrically connected.

A first regulator 53*a*A as shown in FIG. 14 regulates the voltage supplied to the LED substrate 26A at a predetermined voltage value. Furthermore, a second regulator 53*a*A regulates the voltage supplied to the pressure sensor 51 at a predetermined voltage value. A thermocouple may be used as the temperature sensor 52A shown in FIG. 14, for example. In the case where a thermocouple is used, since no power supply is required, only an output section is provided.

The following is a description of the operation of the endoscope 3A of the present embodiment, which has the above-described structure.

The LED illuminators 22A emit light by receiving power from the battery 65A. As a result, a region to be observed is illuminated by illumination light generated from the LED illuminators 22A with the optimum illumination amount for the observation conditions.

In these lighting conditions, the temperature inside the tip section body 2*a* increases due to the heat from the LED illuminators 22A. The temperature increase at this time is measured by the temperature sensor 52A, and the measured value is transmitted to the temperature measuring section 67A. Accordingly, even an operator who is a distance away from the inside of the tip section body 2a can be aware of the temperature change in the inside of the tip section body 2a reliably.

When a joystick, serving as a remote controller, which is provided in the operating section 6 (described in FIG. 1), is operated appropriately, air from the cylinder is fed into the fluid chambers 42A of the fluid pressure actuators 30A. Therefore, the fluid chambers 42A in the multi lumen tubes 31A that are pressurised expand slightly in the radial direction while extending in the axial direction. As a result, the bending section 2bA performs a bending operation. At this time, as shown in FIG. 13B, since the fluid chambers 42A and the pressure measurement holes 11eA are communicated by the communicating tubes 69A, the change in the air pressure in the fluid chambers 42A is measured by the pressure sensors 51A, and the measured values are transmitted to the pressure measuring section 66A. Accordingly, even an operator who is a distance away from the inside of the tip section can be aware easily that the air in the cylinder is supplied to the fluid chambers 42A of the fluid pressure actuators 30A reliably. Furthermore, by performing feedback control based on the measured values transmitted to the pressure measuring section 66A, it is also possible to perform bending control of the bending section 2bA.

As described above, by considering the amount of illuminating light, illumination distance, and the like in advance, and mounting an adaptor 20C that is provided with appropriate LED illuminators 22A on the tip section body 2a, it is possible to illuminate a region to be observed with an optimum illumination light amount according to the observation conditions, and to perform observation satisfactorily.

As a result, for example, even if the insertion section 2 is long, failures where the illuminating light is attenuated, and the amount of illuminating light is insufficient, are avoided.

Moreover, by providing a sensor in the adaptor 20C for measuring at least one of the internal environment near the tip section and the external environment near the tip section, of the insertion section 2, it is possible to be aware of the change in the environmental conditions where the insertion section 2 is located while operating.

That is, using the temperature sensor 52A provided in the adaptor 20C, it is possible to continue operation while considering the influence due to the heat generated by the LED illuminators 22A, and similarly, using the pressure sensors 51A provided in the adaptor 20C, it is possible to measure the pressure of the inside of the fluid chambers 42A of the fluid pressure actuators 30A, and perform bending operations.

In the present embodiment, a case is described where ten LED illuminators 22 are provided around the imaging lens cover 21a. However, the number is not limited to ten, and may be determined appropriately according to the amount of illumination light and the illumination distance, being observation conditions.

Figure 15A:
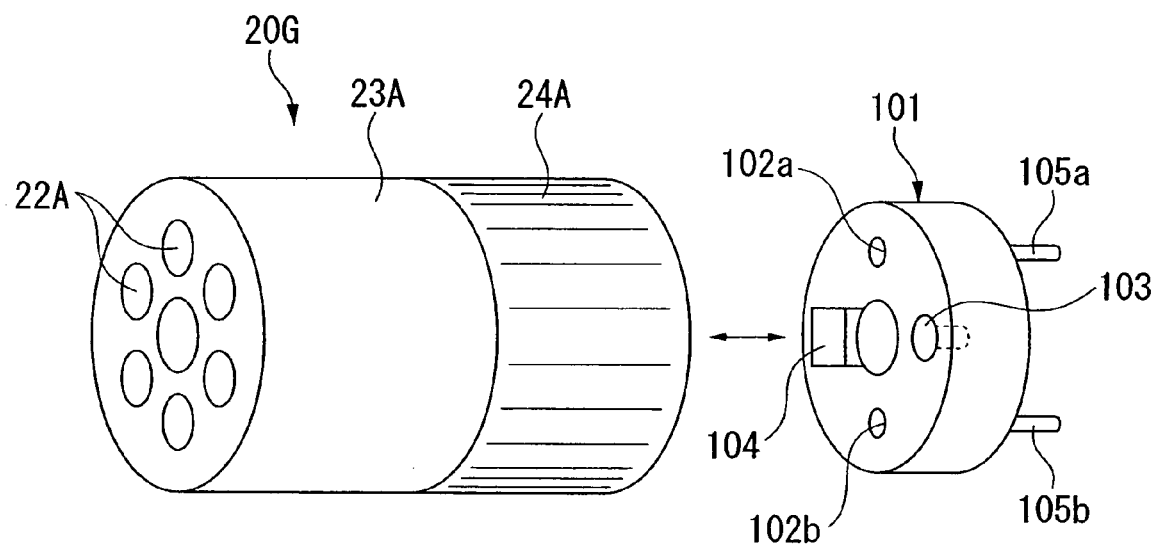
FIGS. 15A and 15B are diagrams showing a modified example of the endoscope apparatus, FIG. 15A being a perspective view of the adaptor, and FIG. 15B being a cross-sectional diagram showing the adaptor mounted onto the insertion section.
Figure 15B:
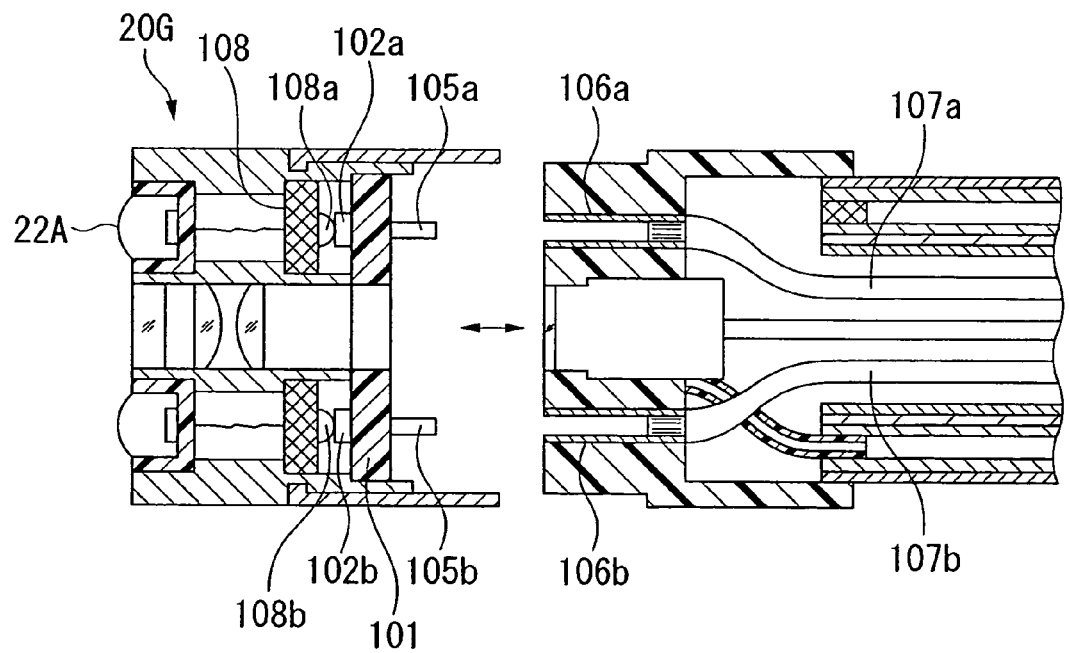

The following is a description of a modified example of the above-described fifth embodiment with reference to FIG. 15A and FIG. 15B. FIG. 15A is a perspective view of an adaptor 20C having a sensor unit, and FIG. 15B is a cross-sectional diagram showing the structure of the adaptor 20G and the tip section body 2a.

The adaptor 20G of the present embodiment is provided with an adaptor body 23A, a connecting tube 24A, and a sensor unit 101, which is attached to and removed from the adaptor body 23. For the sensor unit 101, a plurality of types is prepared, such as one in which a temperature sensor 103 and a pressure sensor 104 are installed, one in which only a pressure sensor 104 is installed, and one in which other sensors are installed, for example, in addition to a pair of electrical contacts 102a and 102b provided in correspondence with LED illuminators 22A. Reference symbols 105a and 105b denote LED illumination unit electrodes protruding from the sensor unit 101. Reference symbols 106a and 106b denote pipe electrodes into which the LED illumination unit electrodes 105a and 105b are inserted. Reference symbols 107a and 107b denote electrical wires extending from the pipe electrodes 106a and 106b. Reference symbol 108 denotes an adaptor substrate. The adaptor substrate 108 of the present embodiment is provided with LED illumination electrical contacts 108a and 108b.

In this manner, by preparing a plurality of types of sensor unit 101 according to the application, it is possible to perform a desired observation without preparing a plurality of adaptors 20G.

Preferred embodiments of the present invention are described above. However, the present invention is not limited to the embodiments. Any structural addition, omission, rearrangement and other modification is possible within the gist of the present invention. The present invention is not limited by the above descriptions, but is only limited by the scope of the appended claims.

The endoscope apparatus described above is summarized as follows.

The first endoscope apparatus of the present invention is provided with: an elongated insertion section; an adaptor, which has an illuminating section and an observation optical system that are attached to and removed from the tip of the insertion section; sensors provided in the adaptor; and electrical contacts for the illumination section, and electrical contacts for the sensor, provided in the adaptor and the tip of the insertion section.

Furthermore, the second endoscope apparatus of the present invention is provided with: an insertion section having an imaging device; an adaptor, which is attached to and removed from the tip section of the insertion section, and has optical lens groups for the illuminating device and for observation; and sensor devices, which are detachably provided between the adaptor and the tip section, or to the front of the adaptor.

According to the second endoscope apparatus, it is possible to install sensor devices, being separate components, such that they can be exchanged between the adaptor and the tip section, or with respect to the tip face of the adaptor. Accordingly, for example, a plurality of adaptors, in which the types of optical lens groups differ, and a plurality of sensor devices, the types and the numbers of which differ, is prepared, and by changing the combinations of the adaptors and sensor devices appropriately, it is possible to assemble an adaptor having a range of types of function easily.

In the above-described second endoscope apparatus, the sensor devices may be provided with one or more types of measuring device, and electrical connection devices for these measuring devices.

In this case, it is possible to supply power to the measuring devices, or supply power to the measuring devices and the illuminating devices, via the sensor devices.

Moreover, the arrangement may be such that the sensor devices are provided between the adaptor and the tip section, the bending section of the insertion section is bent by fluid actuators, and the measuring devices may include pressure sensors for measuring the pressure of the fluid driving the fluid actuators.

In this case, it is possible to perform a range of controls of the fluid actuators using the measured values which is measured by the pressure sensors.

Furthermore, the sensor devices may include memory devices for storing the measured values which is measured by the measuring devices.

In this case, it is possible to obtain a range of information by analyzing the measured values stored in the memory devices after the observation is complete.

Moreover, a sensor information measuring device may be provided for reading information of measured values stored in the memory devices.

In this case, it is possible to analyze the measured values easily at the observation location.

The above-described second endoscope apparatus may be provided with: identification signal output devices, which are provided in both the adaptor and the sensor devices, and output unique signals according to the types of adaptor and sensor devices; and an identification device having a reading and determining device, which reads the unique signals, and determines the types of adaptor and sensor devices.

In this case, it is possible to identify many types of optical lens groups and sensor devices individually, easily and reliably.

As described above, according to the second endoscope apparatus of the present invention, by using appropriate combinations of adaptors and sensor devices, it is possible to assemble a variety of adaptors having different optical lens groups and sensors. Accordingly, it is possible to reduce the types of adaptor to be prepared in advance to the minimum.

In other words, in an endoscope apparatus that requires a plurality of adaptors having different optical lens groups and different sensors depending on the object to be observed and the bending operation system of the bending section, it is possible to share optical lens groups (adaptors containing them) and sensor devices for constructing the adaptors. Accordingly, it is possible to ensure the storage location of the adaptor, and improve portability, and it is also possible to reduce the cost.

What is claimed is:

1. An endoscope apparatus comprising:
   an elongated insertion section which has an imaging device at a tip thereof, and is capable of being connected to an endoscope body at a proximal end thereof;
   an adaptor which has an observation optical system and an illuminating section, and is releasably attached to the tip of the insertion section; and
   an exchange substrate which is exchangeably arranged between the adaptor and the tip of the insertion section, and is provided with at least one sensor,
   wherein the exchange substrate is provided with one or more types of the sensor, and
   an electrical contact which electrically connects with said one or more types of the sensor is provided at the tip of the insertion section.

2. The endoscope apparatus according to claim 1, wherein each of the insertion section and the adaptor is provided with electrical contacts for the illuminating section.

3. The endoscope apparatus according to claim 1, wherein:
   the insertion section is provided with a fluid actuator for controlling a bending section thereof;
   the sensor is a pressure sensor; and
   the pressure sensor measures the pressure of a fluid which drives the fluid actuator.

4. The endoscope apparatus according to claim 1, wherein the exchange substrate is provided with a memory device for storing measured values which are measured by the sensor.

5. The endoscope apparatus according to claim 4, further comprising
   a sensor information measuring device for reading information of the measured values stored in the memory device.

6. The endoscope apparatus according to claim 1, wherein the sensor is at least one of a pressure sensor, a temperature sensor, an acceleration sensor, and a humidity sensor.

7. The endoscope apparatus according to claim 1, wherein the adaptor and the exchange substrate each have a respective corresponding ridge and notch of similar cross-sectional shapes.

8. An endoscope apparatus comprising:
   an elongated insertion section which has an imaging device at a tip thereof, and is capable of being connected to an endoscope body at a proximal end thereof;
   an adaptor which has an observation optical system and an illuminating section, and is releasably attached to the tip of the insertion section; and
   an exchange substrate which is exchangeably arranged between the adaptor and the tip of the insertion section, and is provided with an identification device which outputs a unique identification signal thereof.

9. The endoscope apparatus according to claim 8, wherein the identification device is an IC chip which outputs the unique identification signal thereof.

10. The endoscope apparatus according to claim 9, wherein the type of the adaptor is determined by reading the identification signal from the IC chip.

11. An endoscope apparatus comprising:
    an elongated insertion section which has an imaging device at a tip thereof, and is capable of being connected to an endoscope body at a proximal end thereof;
    an adaptor which has an observation optical system, and is releasably attached to the tip of the insertion section;
    an exchange substrate which is exchangeably arranged between the adaptor and the tip of the insertion section, and is provided with at least one sensor of one or more types, and an electrical contact which electrically connects with said one or more types of the sensor is provided at the tip of the insertion section.

* * * * *